United States Patent
Nguyen

(10) Patent No.: US 6,686,492 B2
(45) Date of Patent: Feb. 3, 2004

(54) PREPARATION OF ORGANOSILICON INTERMEDIATE AND THEIR DERIVATIVES IN A NOVEL GRIGNARD PROCESS

(75) Inventor: Binh T. Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/172,443

(22) Filed: Jun. 13, 2002

(65) Prior Publication Data

US 2003/0233005 A1 Dec. 18, 2003

(51) Int. Cl.$^7$ .................................................. C07F 7/08
(52) U.S. Cl. ......................................................... 556/480
(58) Field of Search ......................................... 556/480

(56) References Cited

U.S. PATENT DOCUMENTS

| | | |
|---|---|---|
| 3,080,324 A | 3/1963 | Richards et al. |
| 3,801,558 A | 4/1974 | Fletcher et al. |
| 4,593,112 A | 6/1986 | Takamizawa et al. |
| 5,596,120 A | * 1/1997 | Bank et al. .................. 556/480 |

OTHER PUBLICATIONS

Coates, et al., Organometallic Compounds, vol. 1, p. 76–103 (1967).
Kirk and Othmer, Enclyclopedia Chemical, vol. 10, p. 721–734 (1966), the Interscience Encyclopedia, Inc., New York, New York.
Turk, et al., Organic Synthesis, vol. 27, 7–8, 1947.

* cited by examiner

*Primary Examiner*—Samuel Barts
(74) *Attorney, Agent, or Firm*—Robert L. McKellar

(57) ABSTRACT

A one-step process for the preparation of organosilicon intermediates. The organosilicon intermediates comprise a group which includes such intermediates as 1,4-bis (dimethylsilyl)benzene, 1,4-bis(dimethylchlorosilyl) benzene, and their derivatives. The process comprises: combining a dihalobenzene with magnesium metal in a co-solvent mixture of an ether and an organic solvent and reacting them with an organosilicon compound of the general formula, R2bHcSiXd. The resulting mixture is allowed to react to completion. The resulting mixture is passed through a filtration device. The liquid, now free of solid magnesium halide, is subjected to a separation technique to recover the subject organosilicon intermediates and their derivatives.

14 Claims, No Drawings

PREPARATION OF ORGANOSILICON INTERMEDIATE AND THEIR DERIVATIVES IN A NOVEL GRIGNARD PROCESS

BACKGROUND OF INVENTION

The present invention is directed to a one step Grignard-type process for preparation of an organosilane. The process comprises contacting a mixture of an organic halide in a co-solvent mixture of an ether and an organic solvent with magnesium metal in an ether and an organic solvent, and reacting this mixture with an organohalosilane. The present inventors have found that the presence of the co-solvent mixture of an ether and an organic solvent provides for a product slurry that stirs and flows easily. These characteristics of the product slurry improve mass transfer and heat transfer during the process and allows for easier separation of the organosilane from the product slurry. Conduct of the present process in the co-solvent provides for improved ratios of the desired organosilane to byproducts and improved recovery of the product from the resultant slurry. Furthermore, the use of the co-solvent allows the process to be run as a continuous process. The process can be self-initiating when it is run with the co-solvent. The process is particularly useful for making bisorganosilylbenzene intermediates.

The reaction of organic halides with magnesium metal in the presence of oxygenated solvents such as dialkyl ethers to form reactive complexes, typically referred to as Grignard reagents, is well known. The production and reactions of Grignard reagents has been the subject of books and numerous review articles. Such reviews are provided, for example, in Coates, et al., ORGANOMETALLIC COMPOUNDS, vol. 1, p. 76–103, (1967), Methuen and Co., LTD, London, U.K., and Kirk and Othmer, ENCYCLOPEDIA CHEMICAL, vol. 10, p. 721–734 (1966), The Interscience Encyclopedia, Inc., New York, N.Y. The structure of the Grignard reagent has not been determined with certainty, however, it is generally believed that the Grignard reagent exists as a complex in solution and that solvent can play a critical role in such complex formation. The unpredictable effect of solvent on the formation and reactivity of the Grignard reagents is discussed in the above cited review articles.

The preparations of organosilicon compounds using a Grignard reagent as an intermediate are known. However, nowhere in the art is there shown the preparation of organosilicon intermediates from a group which includes such intermediates as 1,4-bis(dimethylsilyl)benzene, 1,4-bis(dimethylchlorosilyl)benzene, and their derivatives. Turk et al., Organic Synthesis, vol. 27, 7–8, 1947, teach a process for preparing organic intermediates in anhydrous ether with magnesium turnings. Turk et al. teach that this reaction results in the formation of a thick slurry that becomes unstirrable. This unstirrable slurry is then treated with a hydrochloric acid solution until the magnesium chloride byproduct is in solution and the slurry becomes sufficiently fluid to be stirred.

Such processes as taught by Turk et al. are not generally acceptable as commercial processes. The formation of the unstirrable slurry during the reaction can cause reduced mass transfer and heat transfer, and therefore, reduced yield. Furthermore, the nature of the slurry makes it necessary to treat the slurry in an additional step with a reagent to solubilize the slurry to allow isolation of the product. Typically, a major portion of the product is trapped with the unstirrable slurry. In addition, the nature of the slurry does not allow for the reaction to be run as a continuous process.

It is an objective of the present invention to provide a one step process for preparing organosilanes using a Grignard type reagent as an intermediate, where the process avoids many of the above discussed problems with Grignard type processes by creating a reaction mixture slurry that is flowable and easily stirred. Thus, mass transfer and heat transfer can be improved in the reaction mixture providing for improved yield of organosilane. In addition, the formation of a slurry that is flowable allows for the conduct of the process as a continuous process. No additional steps are necessary to solubilize the slurry to make it flowable and allow for recovery of the organosilane.

The present inventor has found that when an organic halide is contacted with magnesium metal in the presence of a organohalosilane and a co-solvent mixture comprising an ether and a liquid hydrocarbon, the resultant slurry is flowable and easily stirred. Furthermore, yields of the desired organohalosilane are improved due to, for example, improved ratios of the organohalosilane to byproducts and the ability to recover the product from the slurry. The flowable nature of the resulting slurry allows the process to be run as a continuous process.

Richards, et al., U.S. Pat. No. 3,080,324 teach that an oxygenated solvent and a liquid hydrocarbon can be used as a reaction medium in the preparation of a Grignard reagent. Richards, et al., do not teach that their co-solvent system is useful in subsequent reactions of the Grignard reagent with organohalosilanes.

Fletcher, et al., U.S. Pat. No. 3,801,558, teach that advantages can be realized when the reducing agent used in preparing the magnesium-reduced catalyst is an organomagnesium Grignard reagent prepared in a hydrocarbon solvent containing a controlled amount of a complexing agent for the Grignard reagent, such as a dialkyl ether. The reported advantage is that the Grignard reagent may be more soluble in hydrocarbon solvents at ambient temperature. Fletcher, et al., report the use of the Grignard as a reducing agent for titanium trichloride in a process for making a catalyst useful in polymerizing alpha-olefins.

The reaction of Grignard reagents with organohalosilanes is well known and many such reactions are described in Kharash, et al., Grignard Reactions of Nonmetallic Substances, Prentice-Hall, Inc., New York, 1954, p.1306–1331.

Takamizawa, et al., U.S. Pat No. 4,593,112, teach that tert-hydrocarbyl silyl compounds can be synthesized by reacting a tert-hydrocarbylmagnesium halide with a silane compound having at least one silicon-bonded hydrogen atom and at least one silicon-bonded halogen simultaneously in a molecule in a suitable organic solvent. Takamizawa, et al., suggest that the solvent may be a mixture of an ether and an aromatic hydrocarbon solvent.

SUMMARY OF INVENTION

The present invention is a one step Grignard-type process for preparation of organosilanes. The process comprises contacting a mixture of an organic halide in a co-solvent mixture of an ether and an organic solvent with magnesium metal, and reacting this mixture with an organohalosilane. These characteristics of the product slurry improve mass transfer and heat transfer during conduct of the process and allows for easier separation of the organosilane from the product slurry. Conduct of the present process in the co-solvent provides for improvement ratios of the desired organosilane to byproducts and improved recovery of the product from the resultant slurry. Furthermore, the use of the co-solvent allows a process to be run as a continuous process. The process can be self-initiating when run with the co-solvent. The process is particularly useful for making bisorganosilylbenzene intermediates.

DESCRIPTION

The present invention is a one step Grignard-type process for preparation of organosilanes. The process comprises contacting a mixture of an organic halide, described by the formula, $R^1X_a$, in a co-solvent mixture of an ether and an organic solvent with magnesium metal in an ether and an organic solvent, and reacting this mixture with an organohalosilane, described by the formula, $R2bHcSiX_d$, where each $R^2$ and $R^1$ is independently selected from a hydrocarbon group comprising one to about 6 carbon atoms, a=1, 2, or 3, b=0 to 3, c=0 to 3, d=0 to 3, and X is selected group consisting of chlorine and bromine atoms.

By "one step" it is meant that is not necessary to isolate an intermediate Grignard type reagent in the process and further react this Grignard type reagent with organohalosilanes to form the desired organohalosilane intermediate. Furthermore, it is not necessary to conduct a separate solubilization step on the resulting product slurry to facilitate recovery of the organohalosilanes.

For the purposes of the instant invention the term "magnesium metal" is used to generally encompass finely divided magnesium metal in such forms as shavings, chips, powder, and any other physical form that would facilitate easy combination with liquids and facilitate chemical reaction with liquids.

Contact of the magnesium metal with the organic halide and organohalosilane can be effected in standard type reactors suitable for running Grignard type reactions. The reactor can be selected from a group comprising batch type, semi batch type, or continuous type. A preferred reactor is a continuous type reactor. The environment in which the present process is run should be inert. Therefore, in a preferred process the reactor is purged and blanketed with an inert gas such as, for example, nitrogen or argon.

Typically, the magnesium metal and organohalosilane are added to the reactor containing the co-solvent mixture and the organic halide in additional co-solvent is then fed to the reactor at a controlled rate. The mole ratio of magnesium metal fed to the reactor is not critical and can be varied within wide limits. In a batch process it is preferred that the mole ratio of magnesium metal to organic halide provide organic halide in sufficient excess to ensure essentially total conversion of the magnesium metal to magnesium salts. When the present process is conducted as a continuous process, the magnesium metal is typically present in excess in relation to the organic halide fed to the reactor. In such a case, the rate of feed of organic halide and organohalosilane to the reactor can be controlled to assure acceptable levels of conversion of the organic halide to the organohalosilane and minimal presence of unreacted bisorganohalosilylbenzene complexes. The organohalosilane feed may be split, with a portion being added after the magnesium metal bed to insure complete reaction of the organic magnesium halide complex. Any excess organic halide and organohalosilane can be recovered and recycled to the process.

Organic halides useful in the present process are described by the formula, $R^1Xa$, where $R^1$ is a hydrocarbon group comprising about 6 carbon atoms a=1 to 3, and X is selected from a group consisting of chlorine and bromine atoms. The substituent $R^1$ can be a substituted or unsubstituted hydrocarbon group comprising one to 6 carbon atoms. The substituent $R^1$ can be saturated or unsaturated hydrocarbon group comprising one to 6 carbon atoms. $R^1$ can be, for example, alkyl, cycloalkyl, alkenyl, cycloalkenyl, aryl. Specific examples of useful $R^1$ substituents include methyl, ethyl, propyl, tert-butyl, vinyl, allyl, hexenyl, pentyl, phenyl, benzyl, 3,3,3-trifluoropropyl. Preferred organic halides for use in the present process are 1,4-dichlorobenzene and 1,4-dibromobenzene.

Halosilanes useful in the present process are described by the formula, $R^2{}_bH_cSiX_d$, for each $R^2$ is an independently selected hydrocarbon group comprising one to about 6 carbon atoms, b=0 to 3, c=0 to 3, d=0 to 3, and X is selected from a group consisting of chlorine and bromine atoms. The preferred X group is a chlorine atom. The preferred substituent $R^2$ group is selected from a group comprising hydrogen, methyl, ethyl, and phenyl. The halosilane can be, for example, dimethyldichlorosilane, dimethylchlorosilane, methyldichlorosilane, phenylmethyldichlorosilane, phenylmethylchlorosilane, and trimethylchlorosilane.

A preferred process is one in which the magnesium metal present in the process is in excess to the organic halide and halosilane is added in excess to the resulting organic magnesium halide intermediate.

The present process is conducted in the presence of a co-solvent mixture comprising an ether and a liquid aromatic hydrocarbon solvent. The ether can be, for example, diethyl ether, dibutyl ether, tetrahydrofuran, ethylenedimethyl ether, dioxane, or diethylene glycol di-n-butyl ether. The preferred ether is diethyl ether.

The liquid hydrocarbon solvent can be any hydrocarbon solvent that is a liquid under process conditions. The liquid hydrocarbon solvent can be, for example, pentane, hexane, cyclopentane, cyclohexane, toluene, xylene, or benzene. A preferred liquid hydrocarbon solvent is toluene.

The product of the present process is an organosilane in a stirrable slurry. The organosilanes that can be produced by the present process are described by the formula, $(R^2rHsXtSi)eR^1q$. In the formula, each $R^2$ and each $R^1$ is an independently selected hydrocarbon group comprising one to about 6 carbon atoms, q=0 to 2, r=0 to 3, s=0 to 3, t=0 to 3, e=1 or 2, and X is selected from a group consisting of chlorine and bromine atoms. Examples of preferred organosilanes include 1,4-bis(dimethylsilyl)benzene, 1,4-bis(dimethylchlorosilyl)benzene, and their derivatives.

In addition to the organosilane, the slurry can comprise diethyl ether, hydrocarbon solvent, magnesium halide salts, unreacted magnesium metal, and other solids. The organosilane can be further isolated by separating the slurry into a liquid fraction and a solid fraction containing magnesium halide salts, unreacted magnesium metal, and other solids. Such separation can be effected by standard means for separating liquids from solids such as settling or filtration. The liquid portion comprising the organosilane in the co-solvents can be further separated by, for example, distillation to separate the co-solvents from the organosilane. The co-solvents may be recycled to the process.

The following examples are provided to illustrate the present invention and are not intended to limit the scope of the present claims.

EXAMPLE 1 (Not Within the Scope of the Present Invention)

A coupling reaction of $PhMgCl/MeSiCl_3$ to yield PhMeSiCl$_2$ was performed in the presence of diethyl ether (Et$_2$O) as solvent. The Grignard solution in diethyl ether had a mole ratio of 1 mole PhMgCl, 4 moles Et 2O, 3 moles MeSiCl$_3$.

The Grignard was added to a reaction vessel, with an inert atmosphere over a period of thirty-two minutes. The exothermic temperature was allowed to reach a maximum. When agitation was stopped, a "pasty" reaction mixture resulted. Filtration was difficult with this "mashed potatoes" reaction mixture. Toluene was added to this reaction mixture; the magnesium chloride solids separated from the liquid, making filtration possible.

EXAMPLE 2

The above experiment was carried out in a similar procedure, with the exception that portions of toluene were added into the mixture of PhMgCl, $Et_2O$, and $MeSiCl_3$ before the chemical reaction began and during the course of the reaction. The reactants were combined in a mole ratio of: 1 mole PhMgCl/2 mole $Et_2O$/2 mole toluene/3 mole $MeSiCl_3$. Once the combined total amount of reactants were added to the reaction vessel and allowed to react to completion, a very flowable reaction mixture was observed. After mixing was stopped, the reaction mixture was divided into separate liquid and solid layers quickly. The magnesium chloride solids were filtered easily.

EXAMPLE 3

Magnesium turnings, 170 g (7 moles), and 400 ml of tetrahydrofuran were added to a system well purged with nitrogen. The magnesium was activated at ambient temperature with a mixture of 10 g of 1,4-dibromobenzene, 20 g of $Me_2SiCl_2$, and 25 g of tetrahydrofuran causing the temperature increase to 37° C. This was followed the by addition of one liter of tetrahydrofuran and 1806.6 g (14 moles) of $Me_2SiCl_2$. This mixture was heated to 55° C. followed by the addition of a solution of 441 g (3 moles) of 1,4-dichlorobenzene in 600 ml of tetrahydrofuran over six hours. Little or no reaction appeared to occur during the first hour as 240 ml of the mixture was added. An instant exotherm was then observed during which there was a heavy reflux at 70° C. for twenty minutes. The magnesium turned black and salts was observed to form during this time. The temperature was then maintained near 70° C. by the addition of the 1,4-dichlorobenzene. At the end of the addition, gas chromatography (GC) showed the presence of considerable 1,4-bis (dimethylchlorosilyl)benzene. After stirring overnight at ambient temperature and heating for an additional three hours near 72° C., GC showed only a trace of additional product. Ring opening products were not observed. After cooling to ambient temperature, 800 ml of pentane was added, followed by rapid filtration through a paper filter. The filter cake was washed with an additional 800 ml of pentane. The filtrate contained 11.6% of the desired product. The majority of the solvent was removed by distillation at atmospheric pressure. The higher boiling fraction was subjected to vacuum distillation at approximately 4mm Hg to a temperature of 192° C. A fraction of 400 g of 1,4-bis (dimethylchlorosilyl)benzene, which is a solid was obtained. Assuming that GC area % was equal to weight %, the yield of 1,4-bis(dimethylchlorosilyl)benzene based upon 1,4-dichlorobenzene was 61.4%.

EXAMPLE 4

A series of runs was made using a co-solvent comprising diethyl ether and toluene, using procedures similar to those utilized in Example 3, to prepare 1,4-bis(dimethylsilyl) benzene from the reaction of either 1,4-dibromobenzene or 1,4-dichlorobenzene and $Me_2HSiCl$.

TABLE I

Summary of Reactants Utilized

| Run No. | Mg (gm.) | Organic Halide (gm) | $Me_2HSiCl$ (gms) | $ET_2O$ (gms) | Toluene (gms) |
|---|---|---|---|---|---|
| 1 | 26.6 | dichlorobenzene, 73.0 | 155.0 | 298.0 | 280.0 |
| 2 | 53.4 | dichlorobenzene, 148.0 | 312.5 | 592.8 | 553.6 |
| 3 | 26.6 | dichlorobenzene, 73.0 | 160.8 | 290.3 | 277.2 |
| 4 | 26.5 | dibromobenzene, 117.6 | 156.8 | 274.6 | 276.2 |
| 5 | 26.5 | dibromobenzene, 118.1 | 189.4 | 197.5 | 280.8 |
| 6 | 26.5 | dibromobenzene, 117.3 | 191.4 | 252.1 | 138.1 |
| 7 | 53.4 | dibromobenzene, 235.0 | 379.7 | 541.6 | 278.7 |

Notes:
For Run Nos. 5, 6, and 7: $Et_2O$ was split between contacting with magnesium and dissolving dibromobenzene
For Run No. 5 toluene was split between dissolving dibromobenzene and mix with $Me_2HSiCl$

TABLE II

Results of Runs

| Run No. | % Conversion to Silane Products |
|---|---|
| 1 | 87.4 |
| 2 | 86.6 |
| 3 | 89.5 |
| 4 | 90.5 |
| 5 | 89.3 |
| 6 | 84.7 |
| 7 | 90.0 |

What is claimed is:

1. A one-step process for the preparation of organosilane intermediates, the process comprising:

combining a dihalobenzene in a co-solvent mixture of an ether and an organic solvent, wherein the dihalobenzene is described by the formula $R^1X_a$, with magnesium metal in an ether and an organic solvent, and reacting the combination with an organohalosilane of the formula, $R^2{}_bH_cSiX_d$ wherein $R^1$ benzene, X is selected from the group consisting of bromine and chlorine, $a$ has a value of 2, $R^2$ is independently selected from hydrocarbon groups comprising 1 to about 6 carbon atoms, $b$ has a value of 0 to 3, $c$ has a value of 0 to 3, and $d$ has a value of 0 to 3.

2. A process as claimed in claim 1 wherein the total reaction mixture is allowed to react to completion.

3. A process as claimed in claim 2, wherein the total reaction mixture is passed through a filtration device to remove the resultant solid magnesium halide.

4. A process as claimed in claim 3 wherein the liquid, that is essentially free of solids, is subjected to a separation technique to recover the subject organosilane intermediate.

5. A process as claimed in claim 1 wherein the dihalobenzene is 1,4-dichlorobenzene.

6. A process as claimed in claim 1 wherein the dihalobenzene is 1,5-dibromobenzene.

7. A process as claimed in claim 1 wherein the ether is selected from the group consisting of diethyl ether, dibutyl ether, tetrahydrofuran, ethylenedimethyl ether, dioxane, and diethylene glycol di-n-butyl ether.

8. A process as claimed in claim 1 wherein the organic solvent is a hydrocarbon solvent selected from the group consisting of pentane, hexane, cyclopentane, cyclohexane, toluene, xylene, and benzene.

9. A process as claimed in claim 1 wherein the organohalosilane is selected from a group consisting of $Me_2HSiCl$, $MeHSiCl_2$, $Me_2SiCl_2$, $Me_3SiCl$, $PhMeSiCl_2$, $Ph_2MeSiCl$, and $PhMeHSiCl$.

10. A process as claimed in claim 1 wherein the dihalobenzene is 1,4-dichlorobenzene, the ether is diethyl ether, the organic solvent is toluene, and the organohalosilane is $Me_2HSiCl$.

11. A process as claimed in claim 1 wherein the dihalobenzene is 1,4-dichlorobenzene, the ether is diethyl ether, the organic solvent is toluene, the organohalosilane is $Me_2SiCl_2$.

12. A process as claimed in claim 1 wherein the dihalobenzene is 1,4-dibromobenzene, the ether is diethyl ether, the organic solvent is toluene, and the organohalosilane is $Me_2HSiCl$.

13. A process as claimed in claim 1 wherein the dihalobenzene is 1,4-dibromobenzene, the ether is diethyl ether, the organic solvent is toluene, and the organohalosilane is $Me_2SiCl_2$.

14. A process, as claimed in claim 1 wherein the mixture of co-solvents is contacted with the magnesium metal in a continuous flow through a reaction vessel.

* * * * *